United States Patent [19]
Bellini et al.

[11] 4,301,066
[45] Nov. 17, 1981

[54] PREPARATION OF (D-TRP $^6$)-LH-RH VIA THE HEPTAPEPTIDE H-SER-TYR-D-TRP-LEU-ARG-PRO-GLY-NH$_2$

[75] Inventors: Francesco Bellini, Mount Royal; Hans U. Immer, St. Laurent, both of Canada

[73] Assignee: American Home Products Corp., New York, N.Y.

[21] Appl. No.: 147,884

[22] Filed: May 8, 1980

[51] Int. Cl.$^3$ ............................................ C07C 103/52
[52] U.S. Cl. .................... 260/112.5 LH; 260/112.5 R
[58] Field of Search ............................. 260/112.5 LH

[56] References Cited

U.S. PATENT DOCUMENTS 4,003,884  1/1977  König et al. .............. 260/112.5 LH
4,118,483  10/1978  König et al. .............. 260/112.5 LH

FOREIGN PATENT DOCUMENTS 2243066  9/1971  Fed. Rep. of Germany ... 260/112.5 LH

*Primary Examiner*—Delbert R. Phillips
*Attorney, Agent, or Firm*—Arthur E. Wilfond

[57] ABSTRACT

Herein is described a process for preparing the decapeptide Pry-His-Trp-Ser-Tyr-D-Trp-Leu-Arg-Pro-Gly-NH$_2$ ([D-Trp$^6$]-LH-RH) by coupling Pyr-His-Trp-NHNH$_2$ with H-Ser-Tyr-D-Trp-Leu-Arg-Pro-Gly-NH$_2$. [D-Trp$^6$]-LH-RH had been established to be an efficient agent for causing release of lutenizing hormone and follicle-stimulating hormone in mammals.

4 Claims, No Drawings

PREPARATION OF (D-TRP 6)-LH-RH VIA THE HEPTAPEPTIDE H-SER-TYR-D-TRP-LEU-ARG-PRO-GLY-NH₂

BACKGROUND OF THE INVENTION

This invention relates to a novel and useful process for preparing the decapeptide L-Pyr-L-His-L-Trp-L-Ser-L-Tyr-D-Trp-L-Leu-L-Arg-L-Pro-Gly-NH₂([D-Trp⁶]-LH-RH) and to intermediates therefor.

The naturally occurring decapeptide, Pyr-His-Trp-Ser-Tyr-Gly-Leu-Arg-Pro-Gly-NH₂(LH-RH), was isolated and its structure was elucidated by A. V. Schally et al., Biochem. Biophys. Res. Commun., 43, 393 and 1334 (1971). [D-Trp⁶]-LH-RH has been established to be a useful compound for causing release of luteinizing hormone (LH) and follicle-stimulating hormone (FSH) in a mammal by A. V. Schally and D. H. Coy, U.S. Pat. No. 4,010,125, Mar. 1, 1977, incorporated herein by reference, and D. H. Coy et al., J. Med. Chem., 19, 423 (1976). The above cited U.S. Pat. No. 4,010,125 and the J. Med. Chem. article describe a process for preparing [D-Trp⁶]-LH-RH wherein the decapeptide is prepared by solid-phase methodology using protecting groups on the side chain functional groups. Although the solid-phase is useful for preparing small and experimental quantities of the decapeptide, the yield thereby obtained is low and the method of purifying is time consuming and expensive so that use of this method as a commercial process for the production of a valuable drug is economically prohibitive. Furthermore, a rather large number of preparations of LH-RH and its analogs or derivatives have been reported, for example, H. U. Immer et al., U.S. Pat. No. 3,835,108, issued Sept. 10, 1974. However, it is an accepted fact with those skilled in the art of synthetic peptide chemistry that there is no obvious or analogous method for a good preparation of a decapeptide. The latter statement was confirmed in a realistic fashion when an attempt to prepare the object compound of this invention by an analogous process to that described in U.S. Pat. No. 3,835,108 failed because of extremely low yields. The successful preparation of the peptide or a derivative thereof cannot be designed ahead of time. Using a known preparation of even a close derivative does not guarantee a reasonable synthesis of the desired peptide. The methods of coupling, selection of protecting groups and fragments to be used must be determined by the peptide chemist in each preparation.

It has now been found that the process of this invention produces [D-Trp⁶]-LH-RH in commercial quantities at an economically acceptable cost. Surprisingly, this process involves in the final step a coupling of an unprotected tripeptide with an unprotected heptapeptide. A coupling of a tripeptide with a heptapeptide to prepare LH-RH is described by H. Sievertsson et al., Biochem. Biophys. Res. Commun., 44, 1566 (1971). However, the latter preparation uses a different coupling method and also with protecting groups present during the final coupling. Furthermore, use of the same protecting groups as used in the latter report for the preparation of [D-Trp⁶]-LH-RH would not result in a successful preparation because of complications arising from the presence of the two tryptophane residues.

SUMMARY OF THE INVENTION

Described is a process for preparing the decapeptide of formula Pyr-His-Trp-Ser-Tyr-D-Trp-Leu-Arg-Pro-Gly-NH₂, which comprises coupling the tripeptide of formula Pyr-His-Trp-NHNH₂ and the heptapeptide of formula H-Ser-Tyr-D-Trp-Leu-Arg-Pro-Gly-NH₂ according to the azide coupling method. This method involves (a) reacting a solution at −20° to −10° C. of Pyr-His-Trp-NHNH₂ with an organic nitrite and hydrogen chloride to obtain a solution containing Pyr-His-Trp-N₃, (b) making the solution alkaline with an organic proton acceptor, (c) adding H-Ser-Tyr-D-Trp-Leu-Arg-Pro-Gly-NH₂, (d) allowing the peptide fragments to condense, and (e) isolating Pyr-His-Trp-Ser-Tyr-D-Trp-Leu-Arg-Pro-Gly-NH₂. The heptapeptide intermediate of formula H-Ser-Tyr-D-Trp-Leu-Arg-Pro-Gly-NH₂ is prepared by (a) coupling the dipeptide of formula Boc-Ser(Buᵗ)-Tyr-NHNH₂ and the pentapeptide of formula H-D-Trp-Leu-Arg-Pro-Gly-NH₂ according to the conditions of the azide coupling method to obtain the novel protected heptapeptide of the formula Boc-Ser(Buᵗ)-Tyr-D-Trp-Leu-Arg-Pro-Gly-NH₂ and (b) reacting the latter protected heptapeptide under acidic conditions sufficient to remove the Boc and Buᵗ protecting groups.

DETAILS OF THE INVENTION

In general the abbreviations used herein for designating the amino acids and the protective groups are based on recommendations of the IUPACIUB Commission on Biochemical Nomenclature, see Biochemistry, 11, 1726–1732 (1972). For instance, Pyr, His, Trp, Ser, Tyr, D-Trp, Leu, Arg, Pro and Gly represent the "residues" of 5-oxo-L-proline, L-histidine, L-tryptophan, L-tyrosine, D-tryptophan, L-leucine, L-arginine and L-proline, respectively. The term "residue" refers to a radical derived from the corresponding α-amino acid by eliminating the hydroxyl of the carboxyl group and one hydrogen of the α-amino group.

A number of procedures or techniques for the preparation of peptides have hitherto been well established and found in general textbooks of peptide chemistry; for example K. D. Kopple, "Peptides and Amino Acids", W. A. Benjamin, Inc., New York, 1966, pp. 33–51 and E. Schröder and K. L. Lübke, "The Peptides", Vol. I, Academic Press, New York, 1965, pp. 3–128.

For instance, the functional groups which are not involved in th peptide bond formation reaction are protected by a protecting group or groups introduced prior to the condensation reaction. Examples of protecting groups for an amino group not involved in the peptide bond formation are: the urethane type which includes benzyloxycarbony (represented by Z), t-butoxycarbonyl (represented by Boc), α,α-dimethyl-3,5-dimethoxybenzyloxycarbonyl (represented by Ddz), 2-(4-biphenyl)-isopropyloxycarbonyl (represented by Bpoc), 4-chlorobenzyloxycarbonyl, 4-methoxybenzyloxycarbonyl, 4-nitrobenzyloxycarbonyl, isonicotinyloxycarbonyl, isobornyloxycarbonyl, isopropyloxycarbonyl, or ethoxycarbonyl; the acyl type protecting groups which include formyl, trifluoroacetyl, phthalyl, acetyl (Ac), nitrophenylsulfenyl, or toluenesulfonyl; the alkyl type protecting groups which include triphenylmethyl (or trityl, represented by Trt), trimethylsilyl or benzyl; the preferred protecting group in the process of this invention is t-butoxycarbonyl. The hydroxyl of serine, and tyrosine can be optionally protected by acetyl, tosyl, benzoyl, tert-butyl (represented by Buᵗ) and benzyl; the preferred protecting group is tert-butyl. The carboxylic acid function of a peptide or amino acid can be considered protected by a lower alkyl or lower aralkyl ester, which include methyl (represented by OMe), ethyl (represented by OEt), t-butyl (represented by OBu$^t$), or benzyl (represented by OBzl) esters; and also by substituted hydrazides, which include t-butoxycarbonyl hydrazide (represented by NHNH-Boc), benzyloxycarbonyl hydrazide (represented by NHNH-Z), or α,α-dimethyl-3,5-dimethoxybenzyloxycarbonyl hydrazide (represented by NHNH-Ddz).

A peptide or amino acid is coupled with another peptide or amino acid to form a new peptide by the elimination of water (i.e. dehydrative coupling). More specifically, the hydroxyl portion of a free carboxy group in a peptide or amino acid and a hydrogen atom of the free amino group of the other peptide or amino acid are eliminated to form a new amide bond joining the peptide or amino acid starting materials. To promote facile dehydrative coupling of a peptide free carboxy group with a free amino group of another peptide to form a new peptide bond, the free carboxy group must be activated. Descriptions of such carboxy activating groups are included in the general textbooks of peptide chemistry by Kopple, or Schröder and Lübke, cited above. Examples of carboxy group activating agents for a carboxylic acid are thionyl chloride, thionyl bromide, methyl chloroformate, a dialkylcarbodiimide (e.g., dicyclohexylcarbodiimide); N-hydroxysuccinimide, 2,4,5-trichlorophenol, pentachlorophenol, 4-nitrophenyl or 1-hydroxybenzotriazole in the presence of a dialkylcarbodiimide; and in the case of a hydrazide, the carboxylic group activating agent is nitrous acid. Examples of the activated form of the terminal carboxyl group are acid chloride, anhydride, azide, activated ester, or O-acyl urea of a dialkylcarbodiimide.

The coupling of a peptide or amino acid, having the activated carboxy group, with another peptide or amino acid having a free amino group is conducted in an inert organic solvent at a temperature from −30° C. to about 50° C. For coupling to occur, the amino group must not be protonated. A sufficient amount of an organic proton acceptor is added to the above reaction mixture until the amino group is no longer protonated (usually pH 7.0 to 8.0).

The term "azide coupling method" as used herein refers to the method of activating the terminal carboxy of a peptide fragment as an azide and condensing the latter peptide azide with another peptide having a free amino group. The peptide azide is conveniently prepared by reacting a peptide hydrazide with a reagent which furnishes nitrous acid in situ. Suitable reagents for this purpose include organic nitrites (e.g. t-butyl nitrite and isoamyl nitrite) or alkali metal nitrite salts (e.g. sodium nitrite and potassium nitrite) in the presence of a mineral acid, such as hydrogen chloride or sulfuric or phosphoric acid. The corresponding peptide azide thus obtained is then reacted with a peptide or compound having a free amino group to obtain the desired peptide. Preferred conditions for the azide method of coupling comprise reacting the peptide hydrazide with nitrous acid, generated in situ from an organic nitrite in the presence of a strong acid, preferably hydrogen chloride (pH ranging usually from 0.1 to 2), in an anhydrous inert organic solvent, for example, dimethylformamide, dimethyl sulfoxide, ethyl acetate, methylene dichloride, tetrahydrofuran, dioxane, and the like at −30° C. to 20° C., preferably at about −20° C. to −5° C. for 10 to 30 minutes to obtain the corresponding azide. The peptide azide can be isolated but is preferably allowed to remain in the reaction mixture. Thereafter the azide in the above mixture is reacted with one to two molar equivalents of the peptide unit or compound having the free amino group at temperatures ranging from −30° to 20° C. for about one to two hours and then at 0° to 30° C. for 10 to 30 hours. An acid acceptor, preferably an organic proton acceptor, for example N-ethyldiisopropylamine, N-ethylmorpholine or triethylamine, is present in the reaction mixture in order to make the reaction medium slightly alkaline, preferably pH 7.0 to 9.0. See also the above cited textbooks of Kopple or Schröder and Lübke for additional descriptions of this method.

The terms peptide, polypeptide, tripeptide, hexapeptide, and the like as used herein are not limited to refer to the respective parent peptides but are also used with reference to modified peptides with or without functionalized or protecting groups. The term "peptide" as used herein is used with reference to a peptide with two to ten amino acid residues.

The abbreviation Me represents a methyl group, NHNH$_2$ represents a hydrazide group and N$_3$ represents an azide group.

The term "lower alkanol" as used herein means monohydric alcohols having one to four carbon atoms in a straight or branched chain and includes methanol, ethanol, isopropanol and butanol.

The term "mineral acid" as used herein means the strong inorganic acids and includes hydrochloric, hydrobromic, sulfuric, or phosphoric acid. When the term is used in conjunction with an anhydrous system, anhydrous hydrogen chloride is the preferred mineral acid.

The term "organic nitrite" means the lower alkyl nitrites, for instance, t-butyl nitrite, isoamyl nitrite, and the like.

The term "organic proton acceptor" as used herein includes triethylamine, N-ethylmorpholine, N-ethyldiisopropylamine, pyridine and the like.

PREPARATION OF [D-TRP$^6$]-LH-RH

The dipeptide intermediate of formula Boc-Ser(Bu$^t$)-Tyr-NHNH$_2$ is prepared in the following manner. Condensation of Boc-Ser(Bu$^t$)-OH with H-Tyr-OMe gives the dipeptide, Boc-Ser(Bu$^t$)-Tyr-OMe. Preferably, Boc-Ser(Bu$^t$)-OH is condensed as an active ester, which is prepared by reacting Boc-Ser(Bu$^t$)-OH with about an equivalent amount of each of dicyclohexylcarbodiimide and 1-hydroxybenzatriazole in an inert organic solvent, preferably dimethylformamide, at 0° to 30° C. for one to five hours to obtain the active ester in the solution. To this solution is added a solution of about an equivalent amount of H-Tyr-OMe in an inert organic solvent, preferably dimethylformamide. If H-Tyr-Ome exists as an acid addition salt, then an equivalent amount of an organic proton acceptor, preferably N-ethylmorpholine, should be added. The mixture is stirred at 0° to 30° C. for 10 to 30 hours and Boc-Ser(Bu$^t$)-Tyr-OMe is isolated. Reaction of the latter peptide with four to ten molar equivalents of hydrazine hydrate in an inert solvent, preferably methanol, at 15° to 30° C. for 15 to 30 hours gives Boc-Ser(Bu$^t$)-Tyr-NHNH$_2$.

Condensation of Boc-D-Trp-OH with H-Leu-Arg-Pro-Gly-NH$_2$(H-Leu-Arg-Pro-Gly-NH$_2$ is described by H. U. Immer et al., U.S. Pat. No. 3,835,108, Sept. 10, 1974) gives the pentapeptide Boc-D-Trp-Leu-Arg-Pro-Gly-NH$_2$. This condensation is preferably conducted in the same manner as described above for the condensation of Boc-Ser(Bu$^t$)-OH with H-Tyr-OMe. Removal of the α-amino protecting group (Boc) from the pentapeptide using acidic conditions sufficient to remove the Boc protecting group gives the pentapeptide of formula H-D-Trp-Leu-Arg-Pro-Gly-NH$_2$. Hydrochloric, hydrobromic, sulfuric, phosphoric acid, anhydrous hydrogen chloride, trifluoroacetic acid, alone or in the presence of anisole, and the like can be used for the acidic conditions. The preferred conditions make use of a solution of 5 to 200 molar equivalents of trifluoroacetic acid and 5 to 15 molar equivalents of anisole at 0° to 20° C. for 15 minutes to five hours.

Coupling of the latter pentapeptide with Boc-Ser(-Bu$^t$)-Tyr-NHNH$_2$ according to the azide coupling method gives the heptapeptide of formula Boc-Ser(-Bu$^t$)-Tyr-D-Trp-Leu-Arg-Pro-Gly-NH$_2$. A preferred method of achieving this azide coupling is as follows. The dipeptide hydrazide is dissolved in an inert organic solvent, preferably dimethylformamide, and the mixture is cooled to about −20° to −10° C. A solution of about two to five molar equivalents of a mineral acid in an inert organic solvent, preferably three molar equivalents of hydrogen chloride in ethyl acetate, is added to the above solution, followed by 1.0 to 1.5 molar equivalents of an organic nitrite, for example 1.1 to 1.3 molar equivalents of t-butyl nitrite. The solution is stirred at −20° to −10° C. for 10 to 20 minutes to obtain a solution containing the dipeptide azide Boc-Ser(Bu$^t$)-Tyr-N$_3$. An organic proton acceptor, preferably N-ethyldiisopropylamine, is added until pH 7.1 to 9 is attained. The mixture is cooled to about −30° to −20° C. and a solution of substantially one molar equivalent of the pentapeptide in an inert organic solvent, preferably dimethylformamide, is added to the above solution containing the azide. If required, the solution is adjusted to pH 7.1 to 9 with the organic proton acceptor. The reaction mixture is then stirred at about −20° to −10° C. for one to two hours and then at about 20° to 30° C. for 20 to 30 hours. The resulting heptapeptide Boc-Ser(Bu$^t$)-Tyr-D-Trp-Leu-Arg-Pro-Gly-NH$_2$ is then isolated by conventional methods, for example evaporation, precipitation, chromatography and/or crystallization.

Treatment of the heptapeptide with acidic conditions sufficient to remove the Boc and Bu$^t$ protecting groups, in the same manner as described above, gives the heptapeptide H-Ser-Tyr-D-Trp-Leu-Arg-Pro-Gly-NH$_2$. The preferred acidic conditions involves the use of trifluoroacetic acid in the same manner as described above.

Coupling of this heptapeptide with Pyr-His-Trp-NHNH$_2$ (described in U.S. Pat. No. 3,835,108, cited above) according to the azide coupling method, preferably in the same manner as described above, gives the decapeptide Pyr-His-Trp-Ser-Tyr-D-Trp-Leu-Arg-Pro-Gly-NH$_2$.

If desired, the decapeptide obtained from the reaction can be purified by a variety of methods, for example, treatment with ammonium hydroxide, followed by trituration with an appropriate solvent and/or chromatographic methods.

A preferred method of purification involves the following steps. The decapeptide obtained from the reaction is treated with a solution of ammonium hydroxide in aqueous methanol and the solution is evaporated. The residue is then chromatographed through a column of silica gel using a solution of chloroform-methanol-acetic acid as eluant. The purified decapeptide is subjected to another chromatography using carboxymethyl cellulose and a gradient of aqueous ammonium acetate buffers, preferably 0.01 to 0.10 molar. After lyophilization, [D-Trp$^6$]-LH-RH is obtained as the acetate salt. Conversion of the latter salt to the free base or another salt is achieved by conventional methods. For example a solution of the acid addition salt is passed through an anionic exchange resin (OH$^-$form) to obtain the free base. Another salt of a therapeutically acceptable acid is obtained by reacting the decapeptide with one or more equivalents of the appropriate acid. Examples of preferred non-toxic salts are those with therapeutically acceptable organic acids, e.g. acetic, lactic, succinic, benzoic, salicyclic, methanesulfonic, toluenesulfonic, or pamoic acid, as well as polymeric acids such as tannic acid or carboxymethyl cellulose, and salts with inorganic acids such as the hydrohalic acids, e.g. hydrochloric acid, or sulfuric acid, or phosphoric acid. If desired, a particular acid addition salt is converted into another acid addition salt, e.g., a salt with a non-toxic pharmaceutically acceptable acid, by treatment with the appropriate ion exchange resin in the manner described by R. A. Boissonas et al., Helv. Chim. Acta, 43, 1349 (1960). Suitable ion exchange resins are cellulose based cation exchangers, for example carboxymethylcellulose, or chemically modified, crosslinked dextran cation exchanges, for example those of the Sephadex C type, and strongly basic anion exchange resins, for example those listed in J. P. Greenstein and M. Winitz "Chemistry of the Amino Acids", John Wiley and Sons, Inc., New York and London, 1961, Vol. 3, p. 1456.

The following example illustrates further this invention.

EXAMPLE

Preparation of
L-Pyroglutamyl-L-hisitidyl-L-tryptophyl-L-seryl-L-tyrosyl-D-tryptophyl-L-leucyl-L-arginyl-L-prolyl-glycinamide ([D-TRP$^6$]-LH-RH)

A mixture of Boc-Ser(Bu$^t$)-OH (26 g), dicyclohexylcarbodiimide (28.3 g) and 1-hydroxybenzotriazole (18.6 g) in dimethylformamide (200 ml) was stirred at ice-bath temperature for 60 min and at room temperature for 60 min. A solution of H-Tyr-OMe hydrochloride (23.6 g) and N-ethylmorpholine (14.36 ml) in dimethylformamide (160 ml) was added to the above mixture. The resulting mixture was stirred at room temperature overnight and filtered. The filtrate was evaporated and the residue was dissolved in ethyl acetate. The solution was washed with 5% aqueous citric acid, water, saturated sodium bicarbonate solution, water and brine, dried over anhydrous sodium sulfate, and evaporated to give 39 g of Boc-Ser(Bu$^t$)-Tyr-OMe as an amorphous solid. This dipeptide was crystallized from diethyl ether-hexane to a mp of 109°–111° C.; Anal. Calcd for C$_{22}$H$_{34}$N$_2$O$_7$: C, 60.26% H, 7.82% N, 6.39% and Found: C, 60.68% H, 7.87% N, 6.37% and nmr (CDCl$_3$)δ 1.17 (s, 9H), 1.44 (s, 9H) and 3.67 (s, 3H).

A solution of the latter compound (47.5 g) and hydrazine hydrate (22 ml) in methanol (500 ml) was stirred at room temperature overnight and evaporated. The residue was dissolved in methanol and dietyl ether was added. The precipitate was collected and crystallized from methanol-diisopropyl ether to give 28.35 g of Boc-Ser(Bu$^t$)-Tyr-NHNH$_2$: mp 152°–153° C. and nmr (DMSO-D$_6$)δ 1.08 (s, 9H), 1.35 (s, 9H), 6.55 (d, 2H) and 6.90 (d, 2H).

A solution of Boc-D-Trp-OH (5.5 g), dicyclohexylcarbodiimide (4.05 g) and 1-hydroxybenzotriazole (3.6 g) in dimethylformamide (70 ml) was stirred at ice-bath temperature for 90 min. A solution of H-Leu-Arg-Pro-Gly-NH$_2$ diacetate (10 g, described by H. U. Immer et al., U.S. Pat. No. 3,835,108, cited above) in dimethylformamide (60 ml) was adjusted to pH 8 with N-ethylmorpholine and added to the above solution. The resulting mixture was stirred at room temperature overnight and filtered. The filtrate was evaporated and the residue was dissolved in methanol. Diethyl ether was added and the precipitate was collected and chromatographed on silica gel using chloroform-methanol-35% aqueous acetic acid (5:3:1 v/v). The pure fractions were collected and evaporated. The residue was dissolved in methanol and diethyl ether was added. The precipitate was collected and dried to give 7.8 g of Boc-D-Trp-Leu-Arg-Pro-Gly-NH$_2$; nmr (DMSO-D$_6$)$\delta$ 0.80 (m, 6H) and 1.30 (s, 9H); uv max (methanol) 289 ($\epsilon$=4433) and 281 nm ($\epsilon$=5015); and amino acid analysis: Gly (1.00), Pro (0.98), Leu (0.97), Arg (0.95) and Trp (0.63); and $[\alpha]_D^{25}$ −16.89° (c=1, 1% acetic acid).

A solution of the latter pentapeptide (6.1 g) in anisole (7 ml) and trifluoroacetic acid (83 ml) was stirred under an atmosphere of nitrogen at 0° to 5° C. for 60 min and evaporated. The residue was dissolved in methanol and diethyl ether was added. The precipitate was collected, washed with diethyl ether and dried to give H-D-Trp-Leu-Arg-Pro-Gly-NH$_2$ trifluoroacetate.

To a solution of Boc-Ser(Bu$^t$)-Tyr-NHNH$_2$ (3.68 g) in dimethylformamide (84 ml) at −15° C., was added a solution of hydrogen chloride in ethyl acetate (1.7 N, 12.35 ml), followed by t-butyl nitrite (1.17 ml). After stirring at −15° C. for 15 min, the reaction mixture was cooled to −25° C. and adjusted to pH 7 with N-ethyldiisopropylamine (3.95 ml). To this solution at −20° C. was added a solution of the above H-D-Trp-Leu-Arg-Pro-Gly-NH$_2$ trifluoroacetate and N-ethyldiisopropylamine (1.46 ml) in dimethylformamide (27 ml). The reaction mixture was stirred at −15° C. for 60 min, at ice-bath temperature for 60 min and a room temperature for 18 hr. The solvent was evaporated and the residue was dissolved in methanol. Diethyl ether was added and the precipitate was chromatographed on silica gel using chloroform-methanol-32% aqueous acetic acid (15:4:1 v/v). The pure fractions were combined, evaporated and dried to give 5.4 g of Boc-Ser(Bu$^t$)-Tyr-D-Trp-Leu-Arg-Pro-Gly-NH$_2$; nmr (DMSO-D$_6$)$\delta$ 0.75 (m, 6H), 1.05 (s, 9H) and 1.25 (s, 9H); uv max (methanol) 289 ($\epsilon$=4546) and 279 nm ($\epsilon$=5992); amino acid analysis: Gly (1.00), Arg (0.99), Trp (0.44), Ser (0.70), Pro (0.96), Leu (1.39) and Tyr (1.02); and $[\alpha]_D^{25}$ −7.89° (c=1,1% acetic acid).

A solution of the latter heptapeptide (6.8 g) in anisole (15 ml) and trifluoroacetic acid (285 ml) was stirred under an atmosphere of nitrogen at 0° C. for 30 min and at room temperature for 2 hr and evaporated. The residue was dissolved in methanol and diethyl ether was added. The precipitate was collected, washed with diethyl ether and dried to give H-Ser-Tyr-D-Trp-Leu-Arg-Pro-Gly-NH$_2$ trifluoroacetate.

To a solution of Pyr-His-Trp-NHNH$_2$ (3.19 g, described by H. U. Immer et al., U.S. Pat. No. 3,835,108) in dimethyl sulfoxide (19.5 ml) and dimethylformamide (38 ml) was added a solution of hydrogen chloride in ethyl acetate (2.1 N, 19.5 ml), followed by t-butyl nitrite (0.87 ml). After stirring at −15° C. for 15 min, the reaction mixture was cooled to −25° C. and adjusted to pH 7 with N-ethyldiisopropylamine (7.7 ml). To this solution at −20° C. was added a solution of the above prepared H-Ser-Tyr-D-Trp-Leu-Arg-Pro-Gly-NH$_2$ trifluoroacetate and N-ethyldiisopropylamine (1.2 ml) in dimethylformamide (35 ml). The resulting mixture was stirred at −15° C. for 60 min, at ice-bath temperature for 60 min and at room temperature overnight. After evaporation of the solvent, the residue was dissolved in methanol and diethyl ether was added. The precipitate was collected and dissolved in a solution at 0° to 5° C. of methanol (160 ml) and 28% ammonium hydroxide (20 ml). The solution was stirred at 0° to 5° C. for 30 min and evaporated. The residue was chromatographed on silica gel (1200 g) using chloroform-methanol-32% aqueous acetic acid (5:3:1 v/v) and the pure fractions were combined and evaporated. The residue was then chromatographed through a column of carboxymethyl cellulose using a gradient of aqueous ammonium acetate buffers up to 0.075 M. The pure eluates were lyophilized and the residue was lyophilized three times from water to give 4.4 g of the title decapeptide: amino acid analysis: Gly (1.00), His (1.06), Arg (1.03), Trp (2.25), Ser (0.77), Glu (1.21), Leu (1.03) and Tyr (0.94); uv max (methanol) 289 ($\epsilon$=9440) and 279 nm ($\epsilon$=11670); Anal. Calcd for $C_{64}H_{82}N_{18}O_{13}$: C, 54.83% H, 6.55% N, 16.97% and Found: C, 54.90% H, 6.20% N, 16.80% [corrected for water (4.16%) and acetic acid (7.7%)]; and $[\alpha]_D^{25}$ −7.89° (c=1,1% acetic acid).

We claim:

1. A process for preparing the decapeptide Pyr-His-Trp-Ser-Tyr-D-Trp-Leu-Arg-Pro-Gly-NH$_2$, which comprises (i) coupling the protected dipeptide Boc-Ser(Bu$^t$-)-Tyr-NHNH$_2$ and the unprotected pentapeptide H-D-Trp-Leu-Arg-Pro-Gly-NH$_2$ by the azide coupling method to obtain the protected heptapeptide Boc-Ser(Bu$^t$-)-Tyr-D-Trp-Leu-Arg-Pro-Gly-NH$_2$, (ii) removing the Boc and Bu$^t$ -protecting groups from the protected heptapeptide to leave the unprotected heptapeptide H-Ser-Tyr-D-Trp-Leu-Arg-Pro-Gly-NH$_2$ and thereafter (iii) coupling the unprotected tripeptide Pyr-His-Trp-NHNH$_2$ and the unprotected heptapeptide H-Ser-Tyr-D-Trp-Leu-Arg-Pro-Gly-NH$_2$ by the azide coupling method.

2. The process of claim 1 wherein said azide coupling method for preparing the decapeptide, comprises: (a) reacting a solution at −20° to −10° C. of the unprotected tripeptide Pyr-His-Trp-NHNH$_2$ with an organic nitrite and hydrogen chloride to obtain a solution containing unprotected Pyr-His-Trp-N$_3$, (b) making said solution alkaline with an organic proton acceptor, (c) adding unprotected heptapeptide H-Ser-Tyr-D-Trp-Leu-Arg-Pro-Gly-NH$_2$ to the solution, (d) allowing the peptide fragments to condense, and (e) isolating the unprotected decapeptide Pyr-His-Trp-Ser-Tyr-D-Trp-Leu-Arg-Pro-Gly-NH$_2$.

3. The heptapeptide of the formula H-Ser-Tyr-D-Trp-Leu-Arg-Pro-Gly-NH$_2$.

4. A heptapeptide of the formula Boc-Ser(Bu$^t$)-Tyr-D-Trp-Leu-Arg-Pro-Gly-NH$_2$.

* * * * *